United States Patent [19]

Tashjian

[11] Patent Number: 5,288,484
[45] Date of Patent: Feb. 22, 1994

[54] CATIONIC CELLULOSE DERIVATIVE CONTAINING FATTY QUATERNUM GROUPS IN A PRE-SHAMPOO CONDITIONING COMPOSITION

[76] Inventor: Anne Tashjian, c/o Eastman Kodak Company, Rochester, N.Y. 14650-2201

[21] Appl. No.: 884,964

[22] Filed: May 15, 1992

[51] Int. Cl.$^5$ .................. A61K 7/075; A61K 7/08
[52] U.S. Cl. ........................ 424/71; 424/70; 424/DIG. 2; 132/202
[58] Field of Search .............. 424/70, 71, DIG. 2, 424/47; 514/880, 881; 132/202

[56] References Cited

U.S. PATENT DOCUMENTS

| | | | |
|---|---|---|---|
| 3,288,770 | 11/1966 | Butler | 260/88.3 |
| 3,412,091 | 11/1968 | Moffett | 260/247.1 |
| 3,876,760 | 4/1975 | Nersesian et al. | 424/70 |
| 3,912,808 | 10/1975 | Sokol | 424/71 |
| 3,962,418 | 6/1976 | Birkofer | 424/70 |
| 3,980,091 | 9/1976 | Dasher et al. | 132/7 |
| 4,061,150 | 12/1977 | Dasher et al. | 132/7 |
| 4,175,572 | 11/1979 | Hsiung et al. | 132/7 |
| 4,205,063 | 5/1980 | Khalil et al. | 424/70 |
| 4,237,910 | 12/1980 | Khahil et al. | 132/7 |
| 4,269,824 | 5/1981 | Villamarin | 424/70 |
| 4,572,220 | 2/1986 | Hsiung et al. | 424/72 |
| 4,597,962 | 7/1986 | Grollier et al. | 424/71 |
| 4,638,822 | 1/1987 | Grollier | 132/7 |
| 4,847,076 | 7/1989 | Deshpande et al. | 424/71 |
| 4,911,919 | 3/1990 | Patel et al. | 424/70 |
| 4,950,468 | 8/1990 | Nakamura | 424/71 |
| 4,970,067 | 11/1990 | Panandiker et al. | 424/70 |
| 4,978,526 | 12/1990 | Gesslein | 424/70 |
| 5,034,219 | 7/1991 | Deshponde et al. | 424/71 |

FOREIGN PATENT DOCUMENTS

| | | |
|---|---|---|
| 0181547A2 | 5/1986 | European Pat. Off. |
| 3347189A | 5/1984 | Fed. Rep. of Germany |
| 032668 | 10/1978 | Japan |
| 2452248 | 6/1986 | Japan |

OTHER PUBLICATIONS

Jones, R. T. et al., "The behaviour of cationic cellulose derivatives containing fatty quat groups." International Journal of Cosmetic Science, vol. 10, (1988) pp. 219-229.

*Primary Examiner*—G. S. Kishore
*Attorney, Agent, or Firm*—Judith A. Roesler

[57] ABSTRACT

A pretreatment conditioner comprising an aqueous system of from about 0.1 to about 20 weight percent of a cationic cellulose derivative quaternized with fatty $C_{10}$–$C_{18}$ alkyl groups, from about 0.05 to about 20 weight percent of a quaternary polymer; and (3) from about 0.02 to about 10 weight percent of a quaternary ammonium salt, with each weight percentage reflecting the active weight percent of the ingredient, based on the total weight of the composition. The composition is useful in a method of pretreatment conditioning of hair comprising applying to hair the composition followed by shampooing with an anionic shampoo.

8 Claims, 1 Drawing Sheet

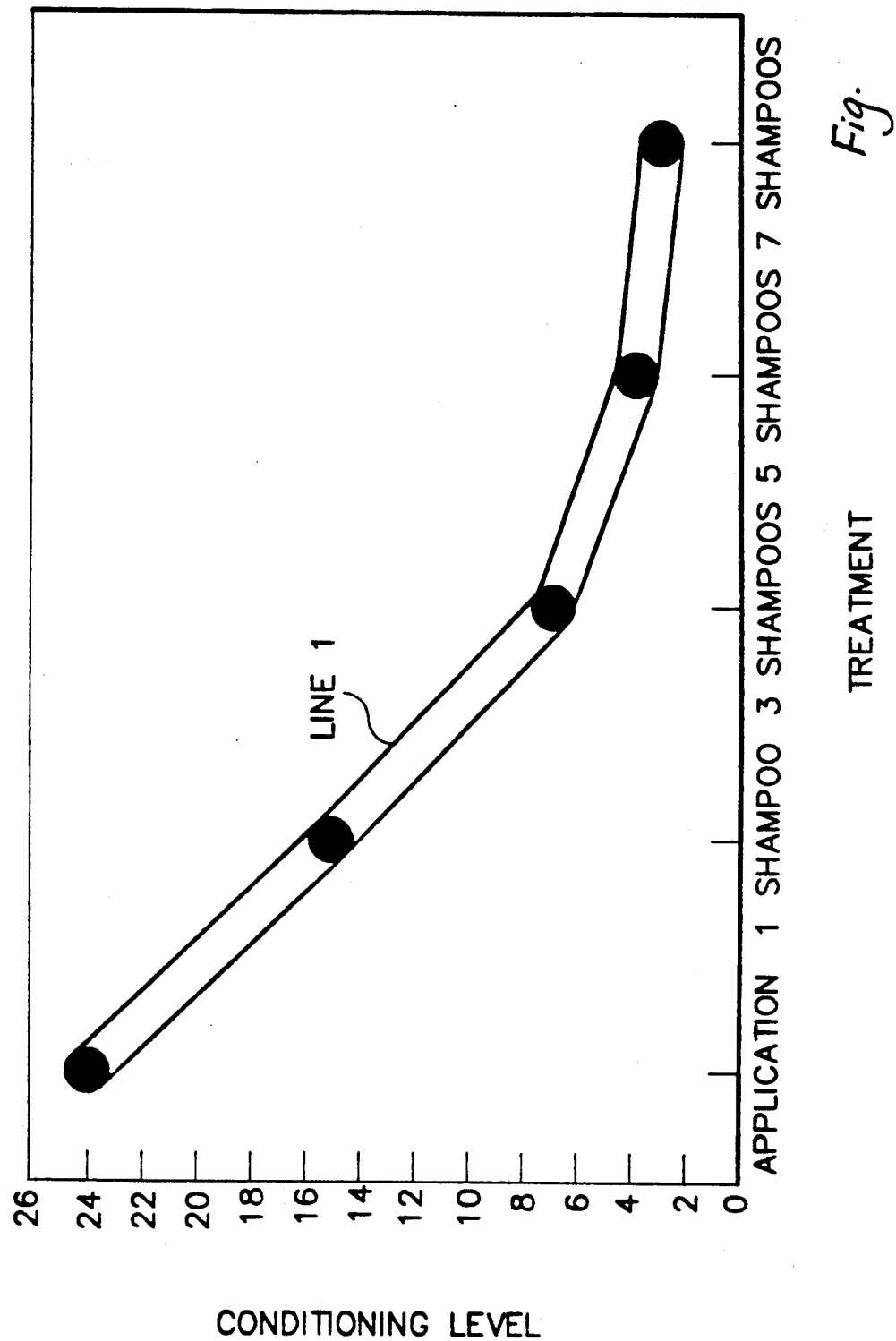

CATIONIC CELLULOSE DERIVATIVE CONTAINING FATTY QUATERNUM GROUPS IN A PRE-SHAMPOO CONDITIONING COMPOSITION

FIELD OF THE INVENTION

This invention relates to hair conditioning compositions and more specifically relates to compositions and methods useful for the pretreatment conditioning of hair before shampooing with an anionic shampoo.

BACKGROUND OF THE INVENTION

Compositions for the pretreatment conditioning of hair have become increasingly popular in recent years. Pretreatment conditioning is particularly useful for chemically treated hair, such as permed or color treated hair. The conditioning effect ideally accomplished by the pretreatment compositions is defined as an improvement of at least one of the following characteristics of the treated hair: softness and smoothness of feel, luster, body or weight, manageability, and combability. The conditioning compositions are generally cationic and therefore best removed by shampooing with an anionic shampoo after the conditioning treatment.

Although pretreatment conditioners offer many advantages, the existing conditioners could be improved both in terms of conditioning effect as well as longevity (defined as the duration of the conditioning effect). A problem in developing new formulations offering increased conditioning effect and longevity is that polymeric build-up on the treated hair often accompanies the extended conditioning effect. The polymeric build-up leaves the hair flattened and dirty looking after the treatment. Discovering a conditioner offering advantages such as an extended conditioning effect without leaving undesirable polymeric build-up is much desired by the hair care industry.

SUMMARY OF THE INVENTION

Pursuant to the present invention, a novel pre-shampoo conditioning composition has been discovered comprising an aqueous system of from about 0.1 to about 20 weight percent of a cationic cellulose derivative quaternized with fatty $C_{10-18}$ alkyl groups; from about 0.05 to about 20 weight percent of a quaternary polymer having recurring units of the formula:

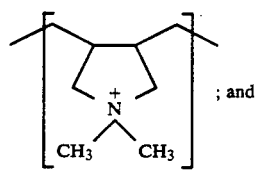

; and from about 0.02 to about 10 weight percent of a quaternary ammonium salt of the formula:

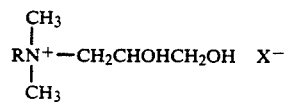

wherein R is an alkyl group of about 7 to about 24 carbon atoms or an alkylamido group of the formula:

wherein R' is an alkyl group of about 7 to about 24 carbon atoms, Y is hydrogen or an alkyl group of 1 to 6 carbons, z is an integer from about 2 to about 6, and X− is a counter-ion selected from the group consisting of a carboxylate group, chloride, bromide, sulfate and phosphate, with the above-mentioned weight percentages reflecting the active weight percent of each ingredient based on the total weight of the composition. The novel conditioning composition is preferably applied to the hair prior to a washing step with an anionic soap or anionic shampoo.

The inventive formulation offers a number of unexpected advantages as a hair conditioner including excellent spreadability, conditioning effect, and longevity of conditioning effect. One or more of the following advantages result when using the novel composition in a hair treatment followed by shampooing, including ease of dry and wet combability of hair, reduction of static, and improvement of body, shine, volume, and fullness of hair. Additionally, the prolonged conditioning effect of the novel composition is accomplished without leaving the hair flattened or dirty looking. Hair treated with the novel composition is left looking clean and easy to style after the treatment and shampooing.

BRIEF DESCRIPTION OF DRAWINGS

FIG. 1 depicts conditioning level on the y axis and the effect of subsequent shampooings on the x axis. Line 1 represents the invention, as more fully discussed in Example IV.

DETAILED DESCRIPTION OF THE INVENTION

The cationic cellulose derivative quaternized with fatty alkyl groups is a water soluble polymer with a cellulose polymer backbone that is quaternized with fatty $C_{10}$–$C_{18}$ alkyl groups. The fatty $C_{10}$–$C_{18}$ alkyl groups are covalently attached to the cellulose polymer backbone. Suitable cellulose polymers forming the polymer backbone include, for example, hydroxyethyl cellulose and hydroxypropyl methyl cellulose, as prepared by methods as known to those skilled in the art. For example, hydroxyethyl cellulose is the product of a reaction between an alkyl cellulose and ethylene oxide, with such products being available in a number of viscosity grades, the selection thereof determining the viscosity of the thus prepared cellulose polymer. The degree of substitution of hydroxyethyl groups per glucose unit in hydroxyethyl celluloses is, for example, preferably 1.4–1.5, and the hydroxyethyl molar substitution is preferably 1.5–3.0. The fatty quaternized alkyl groups may be attached to the cellulose polymer backbone in methods known to one skilled in the art. Preferably the fatty alkyl groups are attached to the cellulose polymer backbone such that one quaternary group is present per anhydro glucose residue. The cellulose derivatives quaternized with fatty alkyl groups employed preferably have a molecular weight ranging from 10,000 daltons to about 1,000,000 daltons, and more preferably less than about 250,000 daltons, and most preferably from about 75,000 to about 125,000 daltons. A preferred cationic cellulose derivative is a coconyl fatty quaternary derivative of hydroxyethyl cellulose ($C_{10}$–$C_{18}$) alkyl dimethyl quat having 1 mole quaternary/anhydro glucose residue, as described in the *International Journal of Cosmetic Science*, Vol. 10, 219–229 (1988). Preferably employed in the present formulation is the commercially available cellulose derivative polymer having the structural representation:

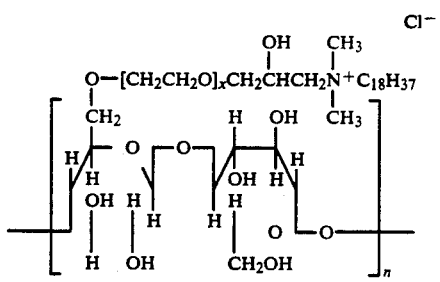

with the CTFA ("CTFA" represents Cosmetic Toiletries Fragrance Association) designation of steardimonium hydroxypropyl oxyethyl cellulose, having a molecular weight of from about 75,000 to about 125,000 daltons, and marketed under the tradename CRODACEL ™ QS (Supplier: Croda, Inc., NY, NY). Although not wishing to be bound by theory, it is believed that the fatty alkyl groups extending from the cellulose polymeric backbone help to effectively attach with the anionic shampoo such that excess conditioner is removed from the treated hair. This is believed to assist in preventing polymeric build-up on the hair.

The cationic polymer quaternized with fatty alkyl groups is preferably employed at a use concentration of from about 0.1 to about 20 weight percent, more preferably from 0.5 to 10 weight percent, and most preferably from 0.7 to 2 weight percent, with each weight percentage reflecting the active weight percent of the polymer, based on the total weight of the composition.

The quaternary polymer of the novel formulation has recurring units of the formula:

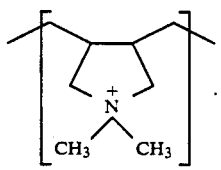

Preferably the polymer is prepared as a homopolymer by polymerizing diallyldimethylammonium chloride or bromide, or other suitable diallyldimethylammonium salts, using a free radical generating polymerization catalyst, such as a peroxide or hydroperoxide, then employing a suitable ion exchange resin, if desired, according to the methods described in U.S. Pat. Nos. 3,288,770 and 3,412,091. The resulting polymers are polydiallyldimethylammonium salts, such as polydiallyldimethylammonium chloride and polydiallyldimethylammonium bromide. A particularly preferred quaternary polymer, is polydiallyldimethylammonium chloride, as recognized by the CTFA name of polyquaternium 6 (as described in the 4th Edition of the *Cosmetic Ingredient Dictionary*) and is available from several commercial sources.

The use concentration of the quaternary polymer identified above preferably falls within the range of from about 0.05 to about 20 weight percent, more preferably from 0.5 to 3 weight percent, and most preferably from 0.65 to 1 weight percent, with each weight percentage reflecting the active weight percent of the polymer, based on the total weight of the composition.

The quaternary ammonium salt employed in the formulation has the formula:

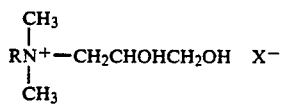

wherein R is an alkyl group of about 7 to about 24 carbon atoms or an alkylamido group of the formula:

wherein R' is an alkyl group of about 7 to about 24 carbon atoms, Y is hydrogen or an alkyl group of 1 to 6 carbons, z is an integer from about 2 to about 6, and X— is a counter-ion selected from the group consisting of a carboxylate group, chloride, bromide, sulfate and phosphate, as described in U.S. Pat. No. 2,589,674 (issued to Cook et al.) and U.S. Pat. No. 4,978,526 (issued to Gesslein et al.). The quaternary ammonium salt is generally water soluble and is unexpectedly useful in both improving the spreadability of the novel composition as well as acting as a conditioner. The most preferred quaternary ammonium salt is identified by the CTFA name of behenamidopropyl dihydroxypropyl PG dimonium chloride and structurally represented by the following formula:

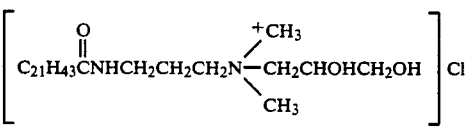

The use concentration of the highly charged salt preferably falls within the range of from about 0.02 to about 10 weight percent, more preferably from 0.05 to 5 weight percent, and most preferably from 0.1 to 0.4 weight percent, with each weight percentage reflecting the active weight percent of the salt, based on the total weight of the composition.

Optional Ingredients

The composition of this invention may include effective amounts of optional ingredients in order to impart additional desirable properties or aesthetic appeal to the composition. As known to those skilled in the art, optional ingredients include, for example, additional hair conditioners, thickeners, preservatives, humectants, vitamins, fragrances, solubilizers for the fragrances, opacifiers, wetting agents, silicones, dyes, surfactants, emollients, sunscreens, botanicals, blends thereof, and so on. Amounts and the blending of these optional ingredients may be included in the formulation by any techniques known to those skilled in the art.

For purposes of ensuring clarity, it is preferred that the composition include at least one low molecular weight monobasic inorganic or organic acid(s), particularly, for example, hydrochloric acid, hydrobromic acid, formic acid, acetic acid, tartaric acid, citric acid, phosphoric acids, or other water-soluble polybasic acids, and so on. The amount of acid included in the formulation is determined such that the composition will have an overall pH falling within the range from about 3 to below or about 7, preferably from 3.5 to 6.0, and most preferably from 3.8 to 4.5. The adjustment of the pH level of the composition can be accomplished by conventional methods known to those skilled in the art.

The hair conditioner compositions are most desirably formulated as aqueous systems employing deionized water. The composition may be formulated in any order at ambient temperatures using conventional mixing techniques known to those skilled in the art, such as stirring or agitating. To ensure homogeneity, the temperature of the formulation may be elevated to range from about 35° C. to about 65° C. The composition may prepared in many different formulations, thus the viscosity of the formulation may be varied greatly, by techniques as known to those skilled in the art. Packaging of the composition may be accomplished in conventional non-pressurized containers, including, for example, squeezable plastic packets or metal tubes.

The pretreatment composition is especially useful in conditioning human hair. Preferably the hair is wetted prior to application of the composition. The composition may be applied at room temperature but preferably is warmed and applied thereafter to the hair. The application to the hair is such that the composition is distributed reasonably thoroughly and uniformly, in any suitable or convenient manner, such as, for example, by massaging the hair for a few minutes with fingers. After massaging the composition, preferably, the hair is rinsed. The treated hair is then washed in a conventional manner with an anionic soap or anionic shampoo. Any of number of known and commercially marketed soaps or shampoos, in liquid, cream or paste form, may be employed containing water-soluble synthetic anionic detergents such as, for example, primary long chain alkyl sulfate salts exemplified by sodium lauryl sulfate or triethanolamine lauryl sulfate or other salts of lauryl sulfate; salts of long chain alkyl benzene sulfonic acids, such as, sodium or triethanolamine salts of linear or branched chain dodecylbenzene sulfonic acids; salts of sulfated monoglyceride such as sodium, ammonium and alkanolamine salts of coconut oil mixed fatty acid monoglycerides; salts of sulfated tridecyl alcohol; or other known anionic synthetic detergents conventionally used in anionic detergent-containing shampoos. The soap or shampoo is then rinsed away with water in the usual manner, with the treated hair ready to be combed and styled as desired.

The following examples are intended to illustrate more fully the nature of the invention without acting as a limitation upon its scope. Other compositions can readily be prepared in light of the disclosure and guiding principles and teachings provided herein to those skilled in the art. Included in the formulations below, for purposes of imparting additional desirable properties were the optional ingredients of: hydroxyethyl cellulose (a thickener), dimethicone copolyol (a silicone surfactant), propylene glycol (a polyhydric alcohol humectant), fragrances, a solubilizer for the fragrances (polysorbate 20), preservatives, dyes, a botanical, and a sunscreen. In the preparation of the compositions illustrated below, hydroxyethyl cellulose was combined with the deionized water and agitated for about 30 minutes prior to the introduction of the other components. The temperatures preceding each listed ingredient are representative of the formulation temperature at the time that each ingredient was included. If no temperature is listed before the ingredients, it is understood that the temperature of the formulation was approximately at room temperature (about 25° C.). The compositions were adjusted to a pH range of between 3.8 to 4.5 employing citric acid (as known to those skilled in the art). The final viscosity of the compositions were within the range of from 500 to 1500 centipoise at 25° C. The steardimonium hydroxypropyl oxyethyl cellulose was obtained under the tradename CRODACEL ™ QS from Croda, Inc., NY, NY. Unless otherwise indicated, the numerical values in the column "Percent by Weight" reflect the active weight percent of the ingredients, If the ingredient was less that 100% active (i.e in an aqueous solution), this is indicated along with the active weight percent below the name of the ingredient.

| Ingredient | Percent by Weight |
|---|---|
| Water (deionized) | q.s. |
| hydroxyethyl cellulose | 0.5% |
| 65° C. polyquaternium 6 (40% active solution, 0.8% active in formula) | 2.0% |
| 65° C. dimethicone copolyol | 2.5% |
| 50° C. propylene glycol | 4.0% |
| 45° C. behenamidopropyl dihydroxypropyl PG dimonium chloride (25% active solution .25% active in formula) | 1.0% |
| 40° C. CRODACEL QS (20% active polymer, 0.8% active in formula) | 4.0% |
| sodium citrate | 0.04% |
| fragrances, solubilizer for fragrances, preservatives, dyes, botanicals, and sunscreen | 5.124% |
| TOTAL COMPOSITION | 100% |

| Ingredient | Percent by Weight |
|---|---|
| Water (deionized) | q.s. |
| hydroxyethyl cellulose | 0.5% |
| 65° C. polyquaternium 6 (40% active solution, 1.6% active in formula) | 2.0% |
| 65° C. dimethicone copolyol | 2.5% |
| 50° C. propylene glycol | 4.0% |
| 45° C. behenamidopropyl dihydroxypropyl PG dimonium chloride (25% active solution .25% active in formula) | 1.0% |
| 40° C. CRODACEL QS (20% active polymer, 0.8% active in formula) | 8.0% |
| sodium citrate | 0.04% |
| citric acid | 0.05% |
| fragrances, solubilizer for fragrances, preservatives, dyes, botanicals, and sunscreen | 5.124% |
| TOTAL COMPOSITION | 100% |

| Ingredient | Percent by Weight |
|---|---|
| Water (deionized) | q.s. |
| hydroxyethyl cellulose | 0.5% |
| 65° C. polyquaternium 6 (40% active solution, 0.8% active in formula) | 2.0% |
| 65° C. dimethicone copolyol | 2.5% |
| 50° C. propylene glycol | 4.0% |
| 45° C. behenamidopropyl dihydroxypropyl | 0.5% |

-continued

| Ingredient | Percent by Weight |
| --- | --- |
| PG dimonium chloride (25% active solution .125% active in formula) | |
| 40° C. CRODACEL QS (20% active polymer, 1.6% active in formula) | 8.0% |
| sodium citrate | 0.04% |
| citric acid | 0.1% |
| fragrances, solubilizer for fragrances, preservatives, dyes, botanicals, and sunscreen | 5.524% |
| TOTAL COMPOSITION | 100% |

EXAMPLE IV

Conditioning Level Testing

To demonstrate the new and unexpected results achieved by the employing the composition of the present invention, the conditioning level of the formulation illustrated in Example III, was measured using a Rubine Dye Test. As shown in the Fig. the inventive formulation (Line 1) showed both a superior conditioning level and longevity, demonstrating a conditioning level lasting beyond one shampooing.

Rubine Dye Test

Preparation of Hair

Eight inch long skeins of natural white virgin human hair were clamped in 1.5 gram sections. A tress was left untreated and three other tresses were then treated with the conditioner formulations described above.

Rubine Dye Test

A 0.5 percent aqueous solution of Direct Fast Rubine WS dye was adjusted to a pH of 3.5 with acetic acid. The tresses treated with the products mentioned above were immersed in the Rubine Dye Solution at 100° F. for five minutes. The tresses were then rinsed thoroughly with room temperature water. The presence of a deep red color indicates cationic active substance has deposited on the tress. In the absence of adsorbed cationic, there is no takeup of the Rubine Dye and thus the hair color remains unchanged. The Rubine Dye Test was conducted on tresses following treatment, following treatment plus one subsequent shampooing (and for the inventive composition treatment plus 1,3,5 and 7 subsequent shampooings). A non-conditioning, anionic shampoo was used.

Measuring the Tresses for Color Difference

In order to quantify the data from the Rubine Dye Test, Minolta's CHROMAMETER ™ Model 200b was utilized to measure color difference between an untreated tress and the treated tresses. This color difference represents the amount of Rubine Dye present on the treated tresses. Color is measured in the three-dimensional L, a and b coordinate system, where L represents color value (lightness), and a and b both represent hue (color) and chroma (vividness). The CHROMAMETER can be programmed to accept one measurement as a baseline and compare it to a second measurement. In this case, the baseline target was the color measurement of the untreated tress and the second measurements were the treated tresses following the Rubine Dye Test. Thus, the instrument takes two points in a three-dimensional coordinate system and calculates the difference by reducing them to a line in a two-dimensional plane utilizing the equation:

$$\Delta E = \sqrt{(L)^2 + (a)^2 + (b)^2}.$$

Each treated tress was measured by averaging three readings and comparing this measurement to the target value (also an average of three readings) of the untreated tress, to obtain $\Delta E$, or the difference in color. The $\Delta E$ was recorded and graphed to show relative results of all the products tested. The larger the $\Delta E$, the larger the color difference, and thus the higher conditioning level effect.

Normalizing the Data

After subjecting an untreated control tress to the Rubine Dye Test, it was discovered that the CHROMAMETER detected a color difference of 5.04 (even though there was no cationic substance deposited on the hair). Thus, in order to normalize the data, this value (5.04) was subtracted from all measurements.

Results

Results indicate that the inventive composition proves a high level of conditioning, with conditioning effects still detectable after subsequent shampooings.

EXAMPLE V

Salon testing on human scalps using half-head studies was performed with the formulation of Example III. The formulation was applied to the hair and followed by a shampooing of the hair with an anionic shampoo. The responses indicated that the formulation was favorable to the panelists in at least one of the following areas: spreadability, feel of product, rinseability, detangling, ease of combing (both wet and dry), manageability, body, sheen, static, residue, or curl spring. Although the inventive formulation received an excellent rating for the conditioning effect, a high overall score was also noted for the response "rinsing easily from your hair". There was no indication that polymeric build-up from the conditioner was problematic to panelist.

The invention has been described in detail with particular reference to preferred embodiments thereof, but it will be understood that variations and modifications can be effected within the spirit and scope of the invention.

That which is claimed:

1. A pre-shampoo conditioning composition comprising an aqueous system of:
   (a) from about 0.1 to about 20 weight percent of a steardimonium hydroxypropyl oxythyl cellulose having a molecular weight of from about 75,000 to about 125,000 daltons;
   (b) from about 0.05 to about 20 weight percent of a quaternary polymer selected from the group consisting of polydiallyldimethylammonium chloride and polydiallyldimethylammonium bromide; and
   (c) from about 0.2 to about 10 weight percent of a dehenamidopropyl dihydroxypropyl dimonium chloride as represented by the formula:

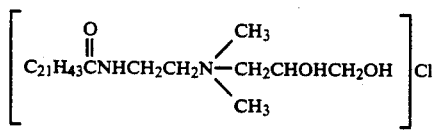

wherein said weight percentages are the active weight percentage of each ingredient, based on total weight of the composition 2. A composition according to claim 1 wherein said (a) is present within a range from about 0.7 to 2 weight percent; (b) is present within a range of 0.65 to 1 weight percent; and (c) is present within a range from 0.1 to 0.4 weight percent.

3. A composition according to claim 1 wherein said (a) is present within a range from 0.5 to 10 weight percent.

4. A composition according to claim 3 wherein said (b) is present within a range from 0.5 to 3 weight percent; and (c) is present within a range from 0.05 to 5 weight percent.

5. A composition according to claim 4 wherein said (b) is present within a range from 0.65 to 1 weight percent; and (c) is present within a range from 0.1 to 0.4 weight percent.

6. A composition according to claim 5 wherein said (b) is polydiallyldimethylammonium chloride.

7. A composition according to claim 6 wherein said (a) is present within a range from 0.7 to 2 weight percent.

8. A method of pretreatment conditioning of hair comprising:
(I) applying to hair a conditioning composition comprising an aqueous system of:
(a) from about 0.1 to about 20 weight percent of a steardimonium hydroxypropyl oxyethyl cellulose;
(b) from about 0.05 to about 20 weight percent of a quaternary polymer selected from the group consisting of polydiallyldimethylammonium chloride and polydiallyldimethylammonium bromide;
(c) from about 0.02 to about 10 weight percent of a behenamidopropyl dihydroxypropyl dimonium chloride as represented by the formula:

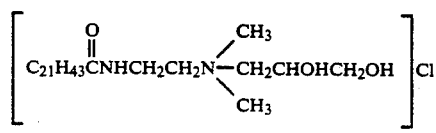

wherein said weight percentages are the active weight percentage of each ingredient, based on total weight of the composition;
(II) shampooing said conditioned hair with an anionic shampoo; and
(III) rinsing said shampoo from hair.

* * * * *